United States Patent [19]
Scarfone et al.

[11] Patent Number: 5,368,046
[45] Date of Patent: Nov. 29, 1994

[54] BONE MARROW NEEDLE ASSEMBLY

[75] Inventors: Frank A. Scarfone, Boca Raton; David Turkel; Alan L. Weisenborn, both of Miami, all of Fla.

[73] Assignee: Symbiosis Corporation, Miami, Fla.

[21] Appl. No.: 36,474

[22] Filed: Mar. 24, 1993

Related U.S. Application Data

[63] Continuation-in-part of Ser. No. 942,427, Sep. 9, 1992.

[51] Int. Cl.$^5$ ............................................. A61B 10/00
[52] U.S. Cl. .................................. 128/754; 604/117
[58] Field of Search ........................... 128/751, 753, 754; 604/117

[56] References Cited

U.S. PATENT DOCUMENTS

| | | | |
|---|---|---|---|
| 2,569,901 | 10/1951 | Richard | 604/117 |
| 3,545,443 | 12/1970 | Ansari | 128/347 |
| 3,850,158 | 11/1974 | Elias et al. | 128/2 B |
| 3,913,566 | 10/1975 | Lacey | 128/2 B |
| 4,022,191 | 5/1977 | Jamshidi | 128/2 B |
| 4,141,365 | 2/1979 | Fischeli et al. | 128/404 |
| 4,142,517 | 3/1979 | Stauropoulos | 128/2 B |
| 4,256,119 | 3/1981 | Gauthier | 128/754 |
| 4,258,722 | 3/1981 | Sessions | 128/753 |
| 4,262,676 | 4/1981 | Jamshidi | 128/753 |
| 4,314,565 | 2/1982 | Lee | 128/753 |
| 4,326,519 | 4/1982 | D'Alo et al. | 128/214.4 |
| 4,356,828 | 11/1982 | Jamshidi | 128/754 |
| 4,403,617 | 9/1983 | Tretinyak | 128/754 |
| 4,430,080 | 2/1984 | Pasquini et al. | 604/240 |
| 4,469,109 | 9/1984 | Mehl | 128/753 |
| 4,487,209 | 12/1984 | Mehl | 128/754 |
| 4,513,754 | 4/1985 | Lee | 128/753 |
| 4,630,616 | 12/1986 | Tretinyak | 128/753 |
| 4,636,201 | 1/1987 | Ambrose et al. | 604/192 |
| 4,655,226 | 4/1987 | Lee | 128/754 |
| 4,793,363 | 12/1988 | Ausherman et al. | 128/754 |
| 4,838,282 | 6/1989 | Strasser et al. | 128/754 |
| 5,005,585 | 4/1991 | Mazza | 128/754 |
| 5,057,085 | 10/1991 | Kopans | 604/173 |
| 5,139,485 | 8/1992 | Smith et al. | 604/158 |

*Primary Examiner*—Max Hindenburg
*Attorney, Agent, or Firm*—David P. Gordon

[57] ABSTRACT

A bone marrow needle assembly includes a cannula housing supporting a cannula having a sharp distal end. The cannula housing is provided with a central throughbore in fluid communication with the cannula and with an ergonomic handle having a curved distal surface. A female luer lock fluid coupling is provided in the housing at the proximal end of the throughbore and within the periphery of the curved handle. A trocar is located within the cannula and extends through the luer lock and the throughbore. The trocar has a cap which extends over the luer lock and is rounded so that a substantially continuous rounded surface is presented by the semi-circular handle and the trocar cap. The distal end of the housing is provided with a threaded portion which receives a locking nut and a depth stop. The depth stop has a mating interior threaded bore which couples with the threaded distal portion of the housing so that the depth stop may be rotated to adjust the effective piercing length of the cannula. The locking nut is rotated into a locking position against the depth stop to secure the depth stop in a selected position.

18 Claims, 2 Drawing Sheets

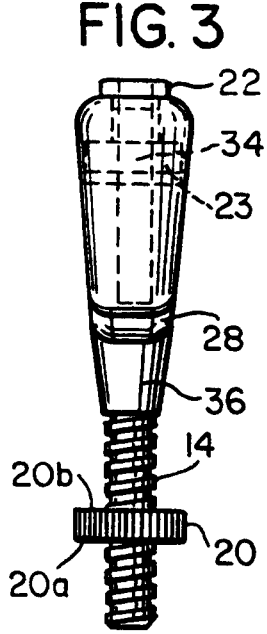
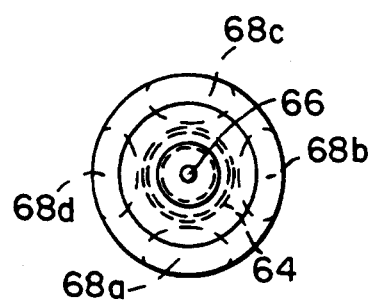
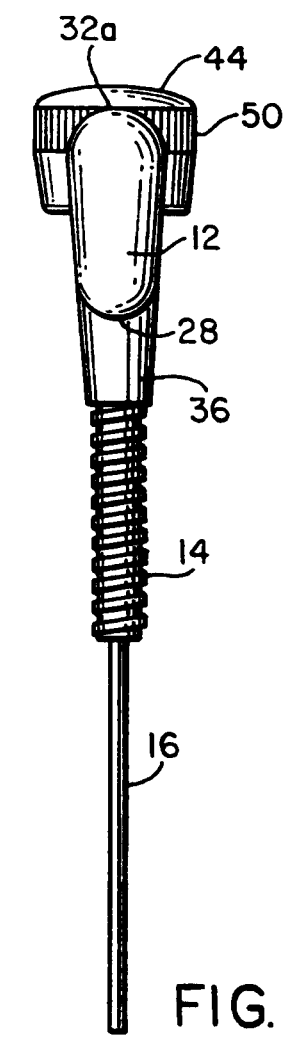
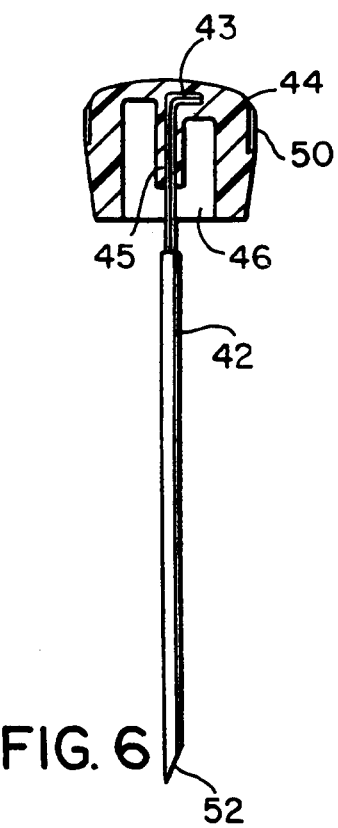
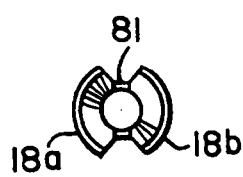
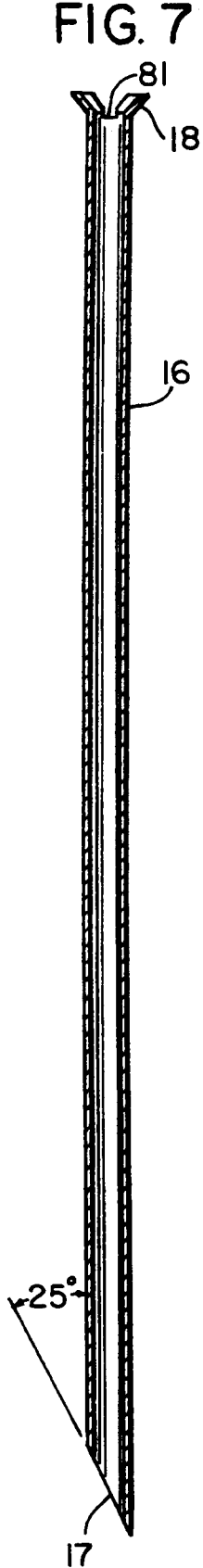

BONE MARROW NEEDLE ASSEMBLY

This application is a continuation-in-part of application Ser. No. 07/942,427 (Coaxial Bone Marrow Biopsy Coring and Aspirating Needle Assembly and Method of Use Thereof) filed Sep. 9, 1992, which is hereby incorporated by reference herein.

BACKGROUND OF THE INVENTION

The invention relates to surgical instruments. More particularly, the invention relates to a needle assembly particularly suited for bone marrow aspiration and intraosseous infusion.

Known biopsy needles generally include a cannula having a lumen extending therethrough, and a trocar or stylet which is removably inserted through the lumen of the cannula. The proximal ends of the cannula and trocar are provided with some type of gripping means and the distal ends of the cannula and trocar are sharpened to a bone piercing edge. In order to aspirate bone marrow or infuse into the bone, the trocar and cannula are forced through the outer hard layer of the bone containing the marrow. Once the softer, internal region of the bone is reached, the trocar is withdrawn and a through-passage to the internal region of the bone is defined by the lumen extending through the cannula.

Early problems with biopsy needles involved the sharpness of the cannula and trocar and the gripping means used so that the needle could be placed accurately and the bone could be penetrated quickly. U.S. Pat. No. 4,356,828, for example, discloses an improved finger gripping member and U.S. Pat. No. 4,403,617 discloses particular cutting edge configurations for the trocar and cannula.

Developments in the gripping means of the trocar and cannula continued with emphasis placed on the secure engagement of the trocar within the cannula and ease of use for the physician. U.S. Pat. Nos. 4,922,602; 4,838,282, 4,793,363 and 4,469,109 for example, disclose fairly elaborate interlocking systems between the trocar gripping means and the cannula gripping means and different shapes for the gripping means.

While some of these biopsy needles are often used for extracting a core sample of bone marrow, most of the biopsy needles are used for aspiration by connecting an aspirating syringe to the proximal end of the cannula and aspirating marrow fluid through the cannula into the syringe. Moreover, these types of needles are sometimes used in pediatrics where an intravenous infusion is difficult because of the small size of an infant's veins. In these applications, an IV bag or the like is attached to the proximal end of the cannula via a fluid conduit and IV fluids are infused directly into bone marrow through the cannula.

In both the aspiration and infusion applications, it is advantageous to provide a fluid connection at the proximal end of the cannula. Moreover, when inserting such a needle into the sternum, it is important to regulate the depth of penetration so that the needle does not protrude through the sternum and into the aorta.

U.S. Pat. No. 4,469,109 to Mehl addresses many of these concerns by providing a bone marrow biopsy needle having a cannula and a cannula housing supporting the cannula. The proximal end of the cannula housing is provided with an angled chamber having a luer taper for receiving a syringe adapter and the distal end of the housing includes a partially threaded portion which engages a threaded depth stop having a flared bottom. By rotating the depth stop relative to the cannula, the piercing length of the cannula is effectively limited. A stylet having a stylet cap supporting the stylet is insertable into the cannula and is lockable in position by interaction of a locking groove in the stylet cap and an outward projection in the cannula housing. The cannula housing is provided with vertical wings extending outward from the housing for gripping by the physician.

Mehl's biopsy needle is an improvement over many of the preceding devices but still presents several problems. Rotation of the threaded depth stop relative to the cannula housing is limited only by whatever frictional resistance may or may not exist between the threads. This can be a substantial disadvantage where the penetration depth of the cannula must be precisely limited. In Mehl's needle assembly, the depth stop could easily rotate out of the desired position causing an unwanted change in the effective piercing length of the cannula. Moreover, the tapered chamber in the proximal end of Mehl's cannula housing provides only a minimal connection for a fluid conduit. This can be a substantial disadvantage when coupling a fluid source to the cannula for a long-term infusion. In particular, the simple luer taper may not be sufficient to securely couple with a fluid conduit from an IV bag or the like. In addition, Mehl's vertical wings, which provide cannula gripping means, are uncomfortable to the physician. This is substantial disadvantage in all bone marrow procedures since the insertion of these needles through bone requires significant effort by the physician.

SUMMARY OF THE INVENTION

It is therefore an object of the invention to provide bone marrow needle assembly with a lockable depth stop.

It is also an object of the invention to provide a bone marrow needle assembly with a secure fluid connection to the cannula.

It is another object of the invention to provide a bone marrow needle assembly having a comfortable ergonomic handle.

In accord with these objects which will be discussed in detail below, the present invention includes a trocar having a trocar cap and a cannula having a cannula housing. The cannula housing has a lower threaded portion and is engageable with a threaded depth stop. A threaded locking nut is provided on the lower threaded portion of the cannula housing so that the position of the housing relative to the depth stop may be locked. The proximal end of the cannula housing is provided with a handle having a substantially semi-circular top surface with a recess for receiving the trocar cap. The top of the trocar cap is rounded so that the trocar cap and the top surface of the handle present a substantially continuous curved surface. In the recess of the handle, and within the periphery of the semi-circular handle, a female luer lock is provided for coupling a fluid conduit or syringe to the cannula when the trocar is removed.

Additional objects and advantages of the invention will become apparent to those skilled in the art upon reference to the detailed description taken in conjunction with the provided figures.

BRIEF DESCRIPTION OF THE DRAWINGS

FIG. 3 is a side view of the needle assembly of FIG. 1 with the trocar, cannula and depth stop removed;

FIG. 4 is a top view of the depth stop element of the needle assembly of FIG. 1;

FIG. 5 is a side view of the needle assembly of FIG. 1 with the depth stop element and locking nut removed;

FIG. 6 is a cross sectional view of the trocar and trocar cap of the needle assembly of FIG. 1;

FIG. 7 is a cross sectional view of the cannula of the needle assembly of FIG. 1; and FIG. 8 is a top view of the proximal end of the cannula of FIG. 7.

DETAILED DESCRIPTION OF THE PREFERRED EMBODIMENTS

Figure 1:
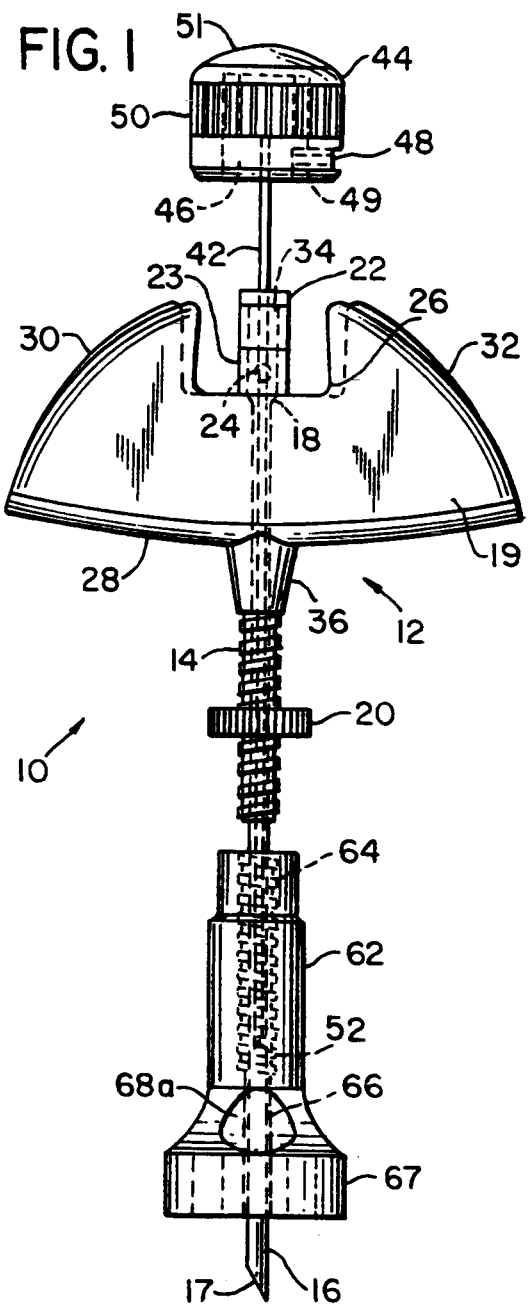
FIGS. 1 and 1a are respectively an exploded and an assembled front view of the needle assembly of the invention.
Figure 1A:
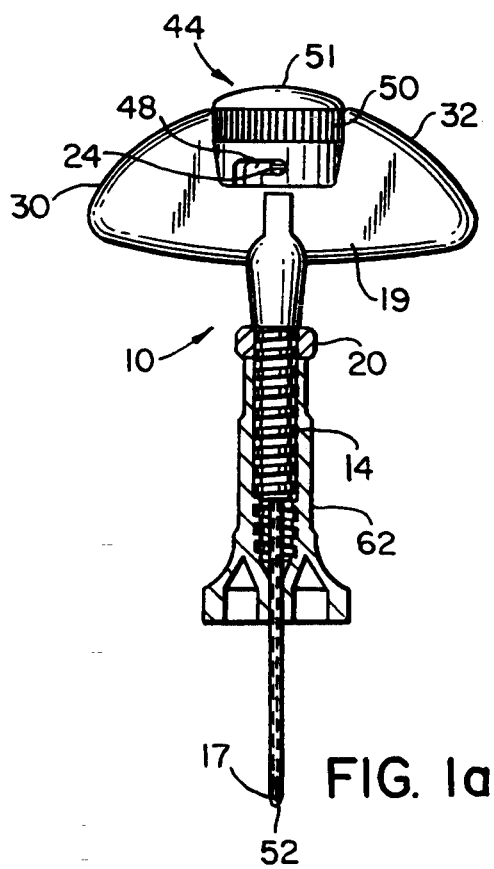

Referring to FIGS. 1-5, the bone marrow needle assembly 10 of the present invention generally includes a cannula housing 12, a cannula 16, a trocar 42, a trocar cap 44, a depth stop element 62 and a depth stop locking nut 20.

The cannula housing 12 has a distal threaded portion 14, an intermediate tapered portion 36 and a proximal handle portion 19. The handle portion 19 is defined by a slightly bowed distal portion 28 and two proximal arcuate portions 30, 32. Arcuate portions 30, 32 substantially define a semi-circle but for the U-shaped recess 26 which separates the arcuate portions 30, 32. Within the U-shaped recess 26, a support 23 is provided which supports a female luer lock 22 and a lateral locking pin 24. A central throughbore 34 extends from the proximal female luer lock through the cannula housing to the end of the distal threaded portion 14. A cannula 16 having a sharpened distal end 17 and a flared proximal end 18, as also seen in FIGS. 7 and 8, is securely seated within throughbore 34.

The trocar 42 is carried by the trocar cap 44. The trocar has a distal end 52 substantially corresponding in shape to the distal end 17 of cannula 16. The trocar 42 is dimensioned to fit snugly inside cannula 16 and to extend substantially the entire length of cannula 16 when the trocar cap 44 is locked into position as shown in FIG. 5. To lock the trocar cap in position, the cap 44 is provided with an internal hollow 46 dimensioned large enough to receive the bushing 23 and the female luer lock 22 of the handle 19. Moreover, the trocar cap 44 is provided with a side slot 48 having a vertical opening 49 (i.e., a bayonet socket) for receiving the lateral locking or bayonet pin 24 of the housing 12. The trocar cap is preferably round in cross-section (as opposed to the handle 19), and a serrated or frictional band 50 surrounding trocar cap 44 allows for easy gripping and twisting of the cap 44 (see FIG. 5). It will be appreciated by those skilled in the art that the trocar 42 is inserted into the cannula 16 via the central through bore 34 while grasping the trocar cap 44 by the frictional band 50. The cap 44 is rotated relative to the handle 19 until the vertical opening 49 aligns with the bayonet pin 26 whereupon the cap is pressed over the luer lock 22 and bushing 23 and twisted until the side slot 48 engages the bayonet pin 24; i.e., to effect locking of the bayonet lock. Those skilled in the art will further appreciate that the trocar is removed from the cannula by substantially reversing this operation.

The trocar cap 44 is further provided with a rounded top surface 51. Thus, with the trocar cap 44 in place on the cannula housing, a substantially smooth and continuous curved proximal surface (comprised of the trocar cap surface 51 and surfaces 30, 32 of handle 19) is presented for fitting in the palm of the hand of the practitioner.

The depth stop element 62 is provided with an internal threaded bore 64 forming part of a central throughbore 66 and a distal flared portion 67. The threaded bore 64 is dimensioned to threadingly mate with the distal threaded portion 14 of the cannula housing 12. The distal flared portion 67 is provided with recesses 68a–68d on its outer surface which aid in rotation of the depth stop 62 relative to the cannula housing 12.

In accord with a preferred aspect of the invention, a locking nut 20 is provided in threaded engagement with the distal threaded portion 14 of the cannula housing 12. The locking nut 20 is threaded onto the distal threaded portion 14 of the cannula housing 12 before the depth stop 62 is similarly attached. It will be appreciated from the above description and especially in connection with FIG. 1, that after the position of the depth stop is selected by rotation of the depth stop about the threaded portion 14 of housing 12, the locking nut 20 is rotated distally until it comes against the depth stop and is tightened to effectively limit movement of the depth stop. To assist rotation and tightening of the locking nut 20, relative to the depth stop element, the locking nut is preferably provided with frictional outer surfaces 20a and 20b. It rill be appreciated by those skilled in the art, that particularly for pediatric infusion, it is important to set the depth stop accurately and maintain that accuracy with the provided locking nut 20.

The overall dimensions of the preferred embodiment of the invention in the assembled condition shown in FIG. 5 are as follows. The entire assembly is approximately 4.4 inches long with the lower threaded portion 14 of the housing 12 being approximately 1.1 inches long and the cannula 16 extending approximately 1.8 inches beyond the threaded portion 14. The depth stop element 62 is preferably also approximately 1.6 inches long and has a narrow proximal diameter of approximately 0.4 inches flaring to a wide distal diameter of approximately 0.9 inches. Thus, it will be appreciated that the positioning of the depth stop relative to the cannula housing can adjust the effective piercing length of the cannula from approximately 1.1 inches to a minimal length (depending on the size and number of threads). The preferred thread pitch for the threaded portion 14 and interior threaded bore 64 is $\frac{1}{4}$ inch $\times$ 16. The locking nut 20 is, of course, dimensioned with the same thread pitch as the threaded bore 64 of the depth stop. The locking nut has a preferred diameter of approximately 0.5 inches and thickness of approximately 0.2 inches.

Figure 2:
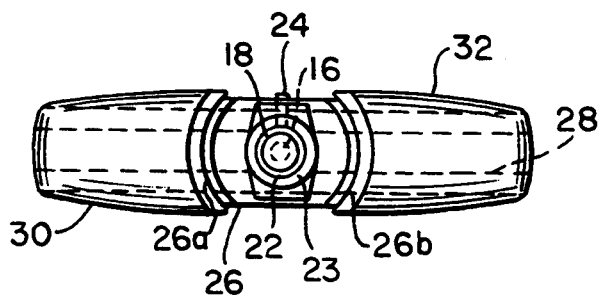
FIG. 2 a top view of the needle assembly of FIG. 1 with the trocar removed.

The arcuate portions 30, 32 of the handle 19 have a preferred radius of approximately 1.375 inches and the U-shaped recess 26 is approximately 0.5 inches deep with curved walls 26a, 26b defined by a diameter of approximately 0.8 inches as seen best in FIG. 2 The bayonet pin 24 is located approximately 0.12 inches from the base of support 23, has a diameter of approximately 0.10 inches and extends approximately 0.18 inches out from the support 23.

The trocar cap 44 is dimensioned to fit comfortably over the female luer lock 22 and mostly within the U-shaped recess 26 (except for at least surface 51) and is therefore dimensioned approximately 0.625 inches tall with a diameter of approximately 0.76 inches. The side slot 48 is approximately 0.1 inches tall by approximately 0.33 inches wide and is located approximately 0.06 inches from the distal end of the cap 44. The vertical opening 49 into the slot 48 is approximately 0.16 inches wide.

As will be appreciated from FIGS. 2, 3, and 5 the handle 19 is tapered and rounded in several directions: from the proximal end to the distal bowed part 28, the handle 19 tapers at an angle of approximately 8°; and from the center to the sides, the handle tapers by a similar amount. The top portions 30a, 32a of the handle are rounded with a radius of approximately 0.275 inches and the bowed portion 28 is rounded with a radius of approximately 0.188 inches. The intermediate tapered portion 36 extends from the bowed portion 28 a length of approximately 0.4 inches with a taper of approximately 4°. This rounded and tapered configuration of the handle 19 has been found to provide a comfortable ergonomic function which makes the needle assembly easier to use.

Details regarding the trocar 42 and cannula 16 are best seen in FIGS. 6–8. The distal ends 17 and 52 respectively of cannula 16 and trocar 42 are sharpened by an angled edge of approximately 25°. The respective outer diameters of the trocar and cannula are approximately 0.045 inches and 0.065 inches. The cannula has an inside diameter of approximately 0.047 inches. The flared proximal end 18 of the cannula extends approximately 0.035 inches at an angle of approximately 45° and is divided into two portions 18a and 18b by a center cutout 81 approximately 0.02 inches wide and 0.01 inches deep. The cannula 16 is secured in the cannula housing 12 by insert molding the cannula 16 therein, while the proximal end 43 of the trocar 42 is secured in the trocar cap 44 by injection molding of the cap with the trocar inserted in the mold. As seen in FIG. 6, the proximal end 43 of trocar 42 has an L-shaped bend which resides in the upper part of the cap and the trocar is surrounded by a central core 45 of the cap 44 defining an annular space 46 for receiving the luer lock 22 shown in FIG. 1.

There has been described and illustrated herein a preferred embodiment of a bone marrow needle assembly. While a single preferred embodiment of the invention has been described, it is not intended that the invention be limited thereto, as it is intended that the invention be as broad in scope as the art will allow and that the specification be read likewise. Thus, while particular dimensions have been disclosed, it will be appreciated that other other dimensions could be utilized without departing from the spirit of the invention. Also, while particular configurations of the depth stop and trocar cap have been shown, it will be recognized that other configurations of the depth stop and trocar cap could be used with similar results obtained. Moreover, while particular configurations have been disclosed in reference to the locking nut, it will be appreciated that other configurations could be used as well so long as the depth stop element may be fixed in place at a desired location and prevented from rotation. In addition, while the invention has been disclosed s having a female luer lock, another locking fluid coupling means could be used instead. It will therefore be appreciated by those skilled in the art that yet other modifications could be made to the provided invention without deviating from its spirit and scope as so claimed.

We claim:

1. A bone marrow needle assembly, comprising:
   a) a cannula housing having a proximal end, a distal end, and forming a central throughbore, said distal end having an outer surface having a threaded portion, said proximal end of said cannula housing being formed as a handle having a proximal outer surface which is curved in a convex manner along an arc having a first radius and a distal outer surface which is bowed in a convex manner along an arc having a second radius, said first radius being smaller than said second radius;
   b) a locking fluid coupling means for mating with one of a fluid injection means and a fluid aspiration means, said locking fluid coupling means being in fluid communication with said central throughbore, said locking fluid coupling means located at said proximal end of said cannula housing;
   c) a locking nut threadably coupled to said threaded portion;
   d) a depth stop means having an interior threaded bore threadably coupled to said threaded portion; and
   e) a cannula mounted in said throughbore of said cannula housing, wherein
   said locking nut is located proximal of said depth stop means on said threaded portion such that rotation of said depth stop about said threaded portion effects a longitudinal movement of said depth stop relative to said housing and rotation of said locking nut effects a longitudinal movement of said locking nut relative to said depth stop means whereby said depth stop means is substantially locked in position by said locking nut when said locking nut is moved against said depth stop means.

2. A bone marrow needle assembly according to claim 1, further comprising:
   f) a trocar which is insertable through said throughbore into said cannula; and
   g) a trocar cap coupled to said trocar and having a first locking means, wherein
   said proximal end of said cannula housing has a second locking means for engaging said first locking means to lock said trocar cap in position whereby said trocar is fixed inside said cannula.

3. A bone marrow needle assembly according to claim 2, wherein:
   a proximal end of said handle has a substantially U-shaped central recess and said locking fluid coupling means is located within said central recess.

4. A bone marrow needle assembly according to claim 3, wherein:
   said trocar cap has a distal end which is substantially circular in cross-section, and
   said U-shaped central recess has arcuate lateral walls which receive said trocar cap.

5. A bone marrow needle assembly according to claim 2, wherein:
   said trocar cap forms an internal hollow which receives said locking fluid coupling means.

6. A bone marrow needle assembly according to claim 5, wherein:
   said first locking means comprises a bayonet socket in said trocar cap; and said second locking means comprises a support with a lateral bayonet pin which mates in said bayonet socket.

7. A bone marrow needle assembly according to claim 2, wherein:
said trocar has an L-shaped proximal end which is insert molded in said trocar cap.

8. A bone marrow needle assembly according to claim 1, wherein:
said locking fluid coupling means is substantially within a periphery of the curve of said proximal outer surface of said handle.

9. A bone marrow needle assembly according to claim 1, wherein:
said handle is tapered from a proximal end to a distal end thereof,
said handle is tapered from a center portion to lateral end portions thereof, and
said handle has smooth rounded edges.

10. A bone marrow needle assembly according to claim 1, wherein:
said locking fluid coupling means is a female luer lock.

11. A bone marrow needle assembly according to claim 1, wherein:
said cannula has a flared proximal end which is insert and molded in said cannula housing.

12. A bone marrow needle assembly according to claim 11, wherein:
said flared proximal end flares at an angle of approximately forty-five degrees, and
said flared proximal end is split into two portions.

13. A bone marrow needle assembly comprising:
a) a cannula housing having a proximal end, a distal end, and central throughbore, said distal end having an outer surface having a threaded portion, said proximal end of said cannula housing being formed as a handle having a proximal outer surface which is curved in a convex manner along an arc having a first radius and a distal outer surface which is bowed in a convex manner along an arc having a second radius, said first radius being smaller than said second radius;
b) a cannula mounted in said throughbore of said cannula housing;
c) a trocar which is insertable through said throughbore into said cannula;
d) a trocar cap coupled to said trocar, with said trocar cap having a first locking means, wherein said cannula has a proximal end having a second locking means for engaging said first locking means to lock said trocar cap in position whereby said trocar is fixed inside said cannula;
e) a locking fluid coupling means in fluid communication with said central throughbore, said locking fluid coupling means located at said proximal end of said cannula housing;
f) a locking nut threadably coupled to said threaded portion of said cannula housing; and
g) a depth stop means having an interior threaded bore threadably coupled to said threaded portion of said cannula housing, wherein
said locking nut is located proximal of said depth stop means on said threaded portion such that rotation of said depth stop means about said threaded portion effects a longitudinal movement of said depth stop relative to said housing and rotation of said locking nut effects a londgitudinal movement of said locking nut relative to said depth stop whereby said depth stop is substantially locked in position by said locking nut when said locking nut is moved against said depth stop.

14. A bone marrow needle assembly according to claim 13, wherein:
said proximal outer surface of said handle forms a central recess, and
said locking fluid coupling means is located within said recess and substantially within a periphery of said curve of said outer surface of said handle.

15. A bone marrow needle assembly according to claim 14, wherein
said trocar cap has a rounded top portion, and said rounded top portion and said curved proximal outer surface of said proximal end of said cannula housing form a substantially continuous rounded outer surface for said bone marrow needle assembly.

16. A bone marrow needle assembly comprising:
a) a cannula housing having a proximal end, a distal end, and forming a central throughbore, said distal end having an outer surface having a threaded portion, said proximal end of said cannula housing being formed as a handle having a proximal outer surface which is curved in a convex manner along an arc having a first radius and a distal outer surface which is bowed in a convex manner along an arc having a second radius, said first radius being smaller than said second radius;
b) a cannula mounted in said throughbore of said cannula housing;
c) a trocar which is insertable through said throughbore into said cannula;
d) a trocar cap coupled to said trocar, with said trocar cap having a first locking means, wherein said cannula has a proximal end having a second locking means for engaging said first locking means to lock said trocar cap in position whereby said trocar is fixed inside said cannula;
e) a locking fluid coupling means in fluid communication with said central throughbore, said locking fluid coupling means located at said proximal end of said cannula housing;
f) a depth stop means having an interior threaded bore threadably coupled to said threaded portion of said cannula housing, wherein
said proximal end of said cannula housing has a central recess therein, and
said locking fluid coupling means is located within said recess, and
said trocar cap has a rounded top portion, and said rounded top portion and said proximal outer surface of said proximal end of said cannula housing form a substantially continuous rounded outer surface for said bone marrow needle assembly.

17. A method of preparing a bone marrow needle assembly for insertion into a bone of a patient, said bone marrow needle assembly having a cannula housing having a proximal end, a distal end, and a central throughbore, said proximal end of said cannula housing being formed as a handle having a proximal outer surface which is curved in a convex manner along an arc having a first radius and a distal outer surface which is bowed in a convex manner along an arc having a second radius, said first radius being smaller than said second radius, said distal end having a first threaded means, a fluid coupling means for mating with one of a fluid injection means and a fluid aspiration means, said fluid coupling means being in fluid communication with said central throughbore, said fluid coupling means located at said proximal end of said cannula housing, a depth stop means having a second threaded means threadably coupled to said first threaded means, a locking means for locking said depth stop means in place, and a cannula mounted in said throughbore of said cannula housing, said method comprising:

a) determining a desired needle length;
 b) rotating said depth stop means relative to said first threaded means until said cannula extends beyond said depth stop means by said desired needle length; and
 c) rotating said locking means into locking engagement with said depth stop means in order to lock said depth stop means in place with said cannula extending beyond said depth stop means by said desired needle length.

18. A bone marrow needle assembly, comprising:

a) a cannula housing having a proximal end, a distal end, and forming a central throughbore;
 b) a locking fluid coupling means for mating with one of a fluid injection means and a fluid aspiration means, said locking fluid coupling means being in fluid communication with said central throughbore, said locking fluid coupling means located at said proximal end of said cannula housing;
 c) a cannula mounted in said throughbore of said cannula housing and being in fluid communication with said locking fluid coupling means, wherein said proximal end of said cannula housing is formed as a handle having a proximal outer surface which is curved in a convex manner along an arc having a first radius and a distal outer surface which is bowed in a convex manner along an arc having a second radius, said first radius being smaller than said second radius.

* * * * *